(12) United States Patent
Ciriello et al.

(10) Patent No.: US 12,370,011 B2
(45) Date of Patent: Jul. 29, 2025

(54) AUTOMATED DENTAL DRILL

(71) Applicant: Cyberdontics (USA), Inc., San Francisco, CA (US)

(72) Inventors: Christopher John Ciriello, Castlegar (CA); James Jackson, Victoria (CA); Nathan John Muller, Victoria (CA); Brian Edward King, Vancouver (CA)

(73) Assignee: Perceptive Technologies, Inc., Boston, MA (US)

( * ) Notice: Subject to any disclaimer, the term of this patent is extended or adjusted under 35 U.S.C. 154(b) by 0 days.

(21) Appl. No.: 17/000,175

(22) Filed: Aug. 21, 2020

(65) Prior Publication Data
US 2020/0390518 A1 Dec. 17, 2020

Related U.S. Application Data

(63) Continuation of application No. PCT/IB2019/000581, filed on May 9, 2019.
(Continued)

(51) Int. Cl.
*A61C 1/00* (2006.01)
*A61B 1/00* (2006.01)
(Continued)

(52) U.S. Cl.
CPC .......... *A61C 1/003* (2013.01); *A61B 1/00193* (2013.01); *A61B 1/24* (2013.01);
(Continued)

(58) Field of Classification Search
CPC ......... A61C 1/00; A61C 1/003; A61C 1/0046; A61C 1/06; A61C 1/082; A61C 1/084;
(Continued)

(56) References Cited

U.S. PATENT DOCUMENTS 3,772,790 A 11/1973 Swan-Gett et al.
4,941,826 A * 7/1990 Loran .................... A61C 1/082
433/215
(Continued)

FOREIGN PATENT DOCUMENTS

CN 105832419 A 8/2016
CN 107205795 A 9/2017
(Continued)

OTHER PUBLICATIONS

Fried et al.: Ablation of Dental Hard Tissues with a Microsecond Pulsed Carbon Dioxide Laser Operating at 9.3-μm with an Integrated Scanner. Proc SPIE Int Soc Opt Eng. 6843:16 pages (2008).
(Continued)

*Primary Examiner* — Edward Moran
(74) *Attorney, Agent, or Firm* — George Jakobsche Patent Counsel PLLC

(57) ABSTRACT

An automated dental drill includes an end effector, including a dental tool for disposition at least partially in a patient's mouth and to perform an operation on a tooth. A tooth clamp releasably rigidly attaches to at least one tooth. A drive assembly is controlled by a processor and positions the end effector with a first at least three degrees of freedom, relative to the tooth clamp. The drive assembly remains outside the patient's mouth. A clamp connector connects the tooth clamp to the drive assembly. With the tooth clamp coupled to the drive assembly and the tooth clamp attached to the at least one tooth, position and orientation of the drive assembly remain fixed, relative to the at least one tooth. A passive cantilever arm, mechanically coupled between a support structure and the drive assembly, has a second at least three degrees of freedom and supports the drive assembly.

15 Claims, 13 Drawing Sheets

Related U.S. Application Data

(60) Provisional application No. 62/830,951, filed on Apr. 8, 2019, provisional application No. 62/755,989, filed on Nov. 5, 2018, provisional application No. 62/669,934, filed on May 10, 2018.

(51) Int. Cl.

| | |
|---|---|
| *A61B 1/24* | (2006.01) |
| *A61B 6/51* | (2024.01) |
| *A61B 34/20* | (2016.01) |
| *A61C 1/06* | (2006.01) |
| *A61C 1/08* | (2006.01) |
| *A61C 3/02* | (2006.01) |
| *A61C 5/82* | (2017.01) |
| *A61B 18/20* | (2006.01) |

(52) U.S. Cl.
CPC .............. *A61B 6/51* (2024.01); *A61B 34/20* (2016.02); *A61C 1/0046* (2013.01); *A61C 1/0061* (2013.01); *A61C 1/06* (2013.01); *A61C 1/082* (2013.01); *A61C 3/02* (2013.01); *A61C 5/82* (2017.02); *A61B 18/20* (2013.01); *A61C 2204/00* (2013.01)

(58) Field of Classification Search
CPC ........... A61C 3/02; A61B 34/20; A61B 34/30; A61B 17/176
See application file for complete search history.

(56) References Cited

U.S. PATENT DOCUMENTS

| | | | |
|---|---|---|---|
| 5,122,060 A | 6/1992 | Vassiliadis et al. | |
| 5,343,391 A | 8/1994 | Mushabac | |
| 5,516,286 A | 5/1996 | Kushner | |
| 6,049,743 A | 4/2000 | Baba | |
| 6,518,033 B1 | 2/2003 | Gromeier et al. | |
| 6,802,713 B1 | 10/2004 | Chishti et al. | |
| 8,251,984 B2 | 8/2012 | Monty | |
| 8,416,984 B2 | 4/2013 | Liang et al. | |
| 8,716,973 B1 | 5/2014 | Lammertse | |
| 9,408,673 B2 | 8/2016 | Monty | |
| 9,554,872 B2* | 1/2017 | Koubi | A61C 1/0007 |
| 9,622,833 B2 | 4/2017 | Monty | |
| 9,675,419 B2 | 6/2017 | Akeel et al. | |
| 9,788,915 B2 | 10/2017 | Monty et al. | |
| 10,016,242 B2 | 7/2018 | Salcedo et al. | |
| 10,052,171 B1* | 8/2018 | Almalki | A61B 1/00091 |
| 2005/0084816 A1* | 4/2005 | Mehdizadeh | A61B 1/24 |
| | | | 433/29 |
| 2005/0193451 A1* | 9/2005 | Quistgaard | A61B 34/76 |
| | | | 901/9 |
| 2006/0127848 A1 | 6/2006 | Sogo et al. | |
| 2006/0177796 A9 | 8/2006 | Heasley | |
| 2007/0265495 A1* | 11/2007 | Vayser | A61B 1/045 |
| | | | 600/109 |
| 2008/0009697 A1 | 1/2008 | Haider et al. | |
| 2008/0153067 A1 | 6/2008 | Berckmans et al. | |
| 2009/0186318 A1 | 7/2009 | Assa et al. | |
| 2009/0248184 A1 | 10/2009 | Steingart et al. | |
| 2010/0105011 A1 | 4/2010 | Karkar et al. | |
| 2011/0143306 A1 | 6/2011 | Hirsch et al. | |
| 2012/0059378 A1 | 3/2012 | Farrell | |
| 2012/0231421 A1 | 9/2012 | Boerjes et al. | |
| 2013/0211242 A1 | 8/2013 | Bertrand et al. | |
| 2013/0322719 A1 | 12/2013 | Dekel et al. | |
| 2014/0272789 A1* | 9/2014 | Mozes | A61B 6/51 |
| | | | 433/173 |
| 2015/0057576 A1 | 2/2015 | Chen | |
| 2015/0057675 A1 | 2/2015 | Akeel et al. | |
| 2015/0320320 A1 | 11/2015 | Kopelman et al. | |
| 2016/0135816 A1 | 5/2016 | Lavallee et al. | |
| 2016/0338803 A1 | 11/2016 | Pesach | |
| 2016/0354169 A1* | 12/2016 | Suttin | A61B 17/3211 |
| 2016/0367336 A1 | 12/2016 | Lv et al. | |
| 2016/0367343 A1* | 12/2016 | Mozes | A61B 34/10 |
| 2017/0079746 A1 | 3/2017 | Sanders | |
| 2017/0319277 A1 | 11/2017 | Cantor-Balan et al. | |
| 2018/0008355 A1* | 1/2018 | Mozes | A61C 1/0015 |
| 2018/0078332 A1* | 3/2018 | Mozes | A61C 1/084 |
| 2018/0185103 A1* | 7/2018 | Mukumoto | A61C 9/0046 |
| 2019/0029524 A1 | 1/2019 | Kopelman et al. | |
| 2019/0076026 A1 | 3/2019 | Elbaz et al. | |
| 2019/0151042 A1 | 5/2019 | Holman et al. | |
| 2020/0315754 A1 | 10/2020 | Ciriello et al. | |
| 2021/0228317 A1 | 7/2021 | Ciriello et al. | |
| 2022/0142736 A1* | 5/2022 | Kim | A61C 1/082 |

FOREIGN PATENT DOCUMENTS

| | | |
|---|---|---|
| DE | 10145104 A1 | 1/2003 |
| EP | 2459115 A2 | 6/2012 |
| FR | 2804859 A1 | 8/2001 |
| RU | 2443396 C1 | 2/2012 |
| WO | WO-2004074324 A2 | 9/2004 |
| WO | WO-2007072866 A1 | 6/2007 |
| WO | WO-2011014802 A2 | 2/2011 |
| WO | WO-2011021192 A1 | 2/2011 |
| WO | WO-2013172919 A1 | 11/2013 |
| WO | WO-2014024157 A1 | 2/2014 |
| WO | WO-2015009856 A2 | 1/2015 |
| WO | WO-2015026546 A2 | 2/2015 |
| WO | WO-2015134633 A1 | 9/2015 |
| WO | WO-2016022347 A1 | 2/2016 |
| WO | WO-2016040657 A1 | 3/2016 |
| WO | WO-2016093984 A1 | 6/2016 |
| WO | WO2017100828 * | 6/2017 |
| WO | WO-2017100828 A1 | 6/2017 |
| WO | WO-2017130060 A1 | 8/2017 |
| WO | WO-2018154485 A1 | 8/2018 |
| WO | WO-2019215511 A2 | 11/2019 |
| WO | WO-2019215512 A1 | 11/2019 |
| WO | WO-2021044218 A1 | 3/2021 |
| WO | WO-2021155045 A1 | 8/2021 |
| WO | WO-2021257708 A1 | 12/2021 |

OTHER PUBLICATIONS

U.S. Appl. No. 16/774,679 Office Action dated Oct. 19, 2020.
PCT/IB2019/000578 International Preliminary Report on Patentability dated Nov. 10, 2020.
Fried et al.: Frailty in older adults: evidence for a phenotype. J Gerontol A Biol Sci Med Sci.; 56(3):M146-56 (2001).
Geomagic Sculpt website http://www.geomagic.com/en/products/sculpt/touch/ (automatically redirected to http://www.geomagic.com/en/products/sculpt/touch/), accessed Oct. 2, 2018.
Yuan et al.: An automatic tooth preparation technique: A preliminary study; Scientific Reports|6:25281|DOI:10.1038/srep25281, pp. 1-9 (2016).
PCT/IB2017/000109 International Preliminary Report on Patentability dated Jul. 31, 2018.
PCT/IB2017/000109 International Search Report and Written Opinion dated Jun. 14, 2017.
PCT/IB2018/051115 International Search Report and Written Opinion dated Jun. 5, 2018.
PCT/IB2019/000578 International Preliminary Report and Written Opinion dated Nov. 18, 2019.
U.S. Appl. No. 16/073,057 Office Action dated Jul. 31, 2019.
Visuri et al.: Shear Strength of Composite Bonded to Er:YAG Laser-prepared Dentin. J Dent Res; 75(1):599-605 (1996).
PCT/US2021/015555 International Search Report and Written Opinion dated Apr. 14, 2021.
U.S. Appl. No. 16/774,679 Final Office Action dated Jul. 21, 2021.
U.S. Appl. No. 17/000,175 First Action Interview dated Jun. 4, 2021.
PCT/US2021/037635 Invitation to Pay Additional Fees dated Aug. 24, 2021.
Kauer et al.: Clinical evaluation of effects of low-level lasers on pain during cavity preparation. International Journal of Research—Granthaalayah. 6(10):81-86 (2018).

(56) References Cited

OTHER PUBLICATIONS

PCT/US2021/037635 International Search Report and Written Opinion dated Nov. 26, 2021.
PCT/US2021/048893 International Search Report and Written Opinion dated Dec. 7, 2021.
PCT/US2021/050413 International Search Report and Written Opinion dated Dec. 23, 2021.
U.S. Appl. No. 16/774,679 Office Action dated Oct. 26, 2021.
European Patent Application No. 18757107.0 European Search Report dated Feb. 4, 2021.
Kim et al.: Improved accuracy in periodontal pocket depth measurement using optical coherence tomography. J Periodontal Implant Sci. 47(1):13-19 (2017).
Le et al.: A non-invasive imaging and measurement using optical coherence tomography angiography for the assessment of gingiva: An in vivo study. J Biophotonics. 11(12) (2018).
PCT/IB2020/000729 International Search Report and Written Opinion dated Dec. 31, 2020.
Tsubokawa et al.: In vitro and clinical evaluation of optical coherence tomography for the detection of subgingival calculus and root cementum. J Oral Sci. 60(3):418-427 (2018).

* cited by examiner

AUTOMATED DENTAL DRILL

CROSS-REFERENCE

This application is a continuation of International Application No. PCT/IB2019/000581, filed on May 9, 2019, which claims the benefit of U.S. Provisional Patent Application No. 62/669,934, filed on May 10, 2018, U.S. Provisional Patent Application No. 62/755,989, filed on Nov. 5, 2018, and U.S. Provisional Patent Application No. 62/830,951, filed on Apr. 8, 2019, each of which is entirely incorporated herein by reference.

BACKGROUND

Although advances have been made in recent years for the treatment of specific dental diseases, the actual delivery of dental treatment remains a manually intensive process. Accordingly, there is a need for methodology for automating dental treatment.

SUMMARY

In at least one aspect, the present invention is related to automated dental drill systems for treating dental disease. The present invention solves one or more problems of the prior art by providing in at least one embodiment, an automated dental drill for performing dental surgery on a subject. The automated dental drill includes a dental drill housing that includes a mouthpiece housing section and a translation drive housing section; an end effector drive support having a shaft section that is at least partially positioned in the mouthpiece housing section, and an end effector for cutting of a native tooth or dental appliance to a desired tolerance. The end effector is positioned on the end effector drive support. The automated dental drill also includes a motor that drives the end effector which is mechanically coupled to the end effector. In an alternative embodiment, the end effector is a cutting laser, connected to a laser generating source through optical means. A drive assembly positions the end effector along three orthogonal linear directions relative to the mouthpiece housing section.

In at least one aspect, the present invention is directed to automated dental drill (ADD) which is a fully automated robotic platform and support system for crown preparations (among others, e.g. bridges, veneers, carious material removal, root canals, etc.) in dental surgeries. The ADD is intended to perform the cutting of a native tooth to a desired tolerance and form, so a prepared prosthetic tooth may be adhered to it, replacing the need for manual cutting currently done by dentists.

One aspect provided herein is an automated dental drill comprising: a dental drill housing that includes a mouthpiece housing section and a translation drive housing section; an end effector drive support having a shaft section that is at least partially positioned in the mouthpiece housing section; an end effector for cutting of a native tooth or dental appliance to a desired tolerance, the end effector positioned on the end effector drive support; a motor that drives the end effector is coupled to the end effector; and a drive assembly to translate the end effector along one or more degrees of freedom relative to the mouthpiece housing section.

In some embodiments, the automated dental drill further comprises a rotation drive positioned in the dental drill housing, the rotation drive rotating the end effector drive support and therefore the end effector with respect to the mouthpiece housing section. In some embodiments, the rotation drive rotates the end effector drive support about an axis through the shaft section. In some embodiments, the shaft section is hollow in order to allow coupling of the motor to the end effector. In some embodiments, the motional drive assembly includes three rotational drives and three translational drives that can move end effector with six degrees of freedom. In some embodiments, the motional drive assembly includes three translational drives that can move end effector in three orthogonal linear directions. In some embodiments, the three translational drives are each independently an electromechanical device (motor, e.g. stepper drive or piezoelectric drive or servomotor drive, etc.). In some embodiments, the three rotational drives and three translational drives are each independently an electromechanical device (motor, e.g. stepper drive or piezoelectric drive or servomotor drive, etc.). In some embodiments, the three translational drives are each independently an electromechanical device (motor, e.g. stepper drive or piezoelectric drive or servomotor drive, etc.). In some embodiments, the dental drill further comprises a coupler that couples movement of the six motional drives to the end effector drive support and end effector. In some embodiments, the dental drill further comprises a coupler that couples movement of the three translational drives to the end effector drive support and end effector. In some embodiments, a portion of the drive mechanism is positioned directly above the end effector, manipulating it in one or more degrees of freedom. In some embodiments, the entire drive mechanism is miniaturized and positioned directly above the end effector, manipulating it in two or more degrees of freedom.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of components. Therefore, specific structural and functional details disclosed herein are not to be interpreted as limiting, but merely as a representative basis for teaching one skilled in the art to variously employ the present invention.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

The term "subject" as used herein refers to a human patient in need of dental treatment.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Dental Drills

Figure 1:
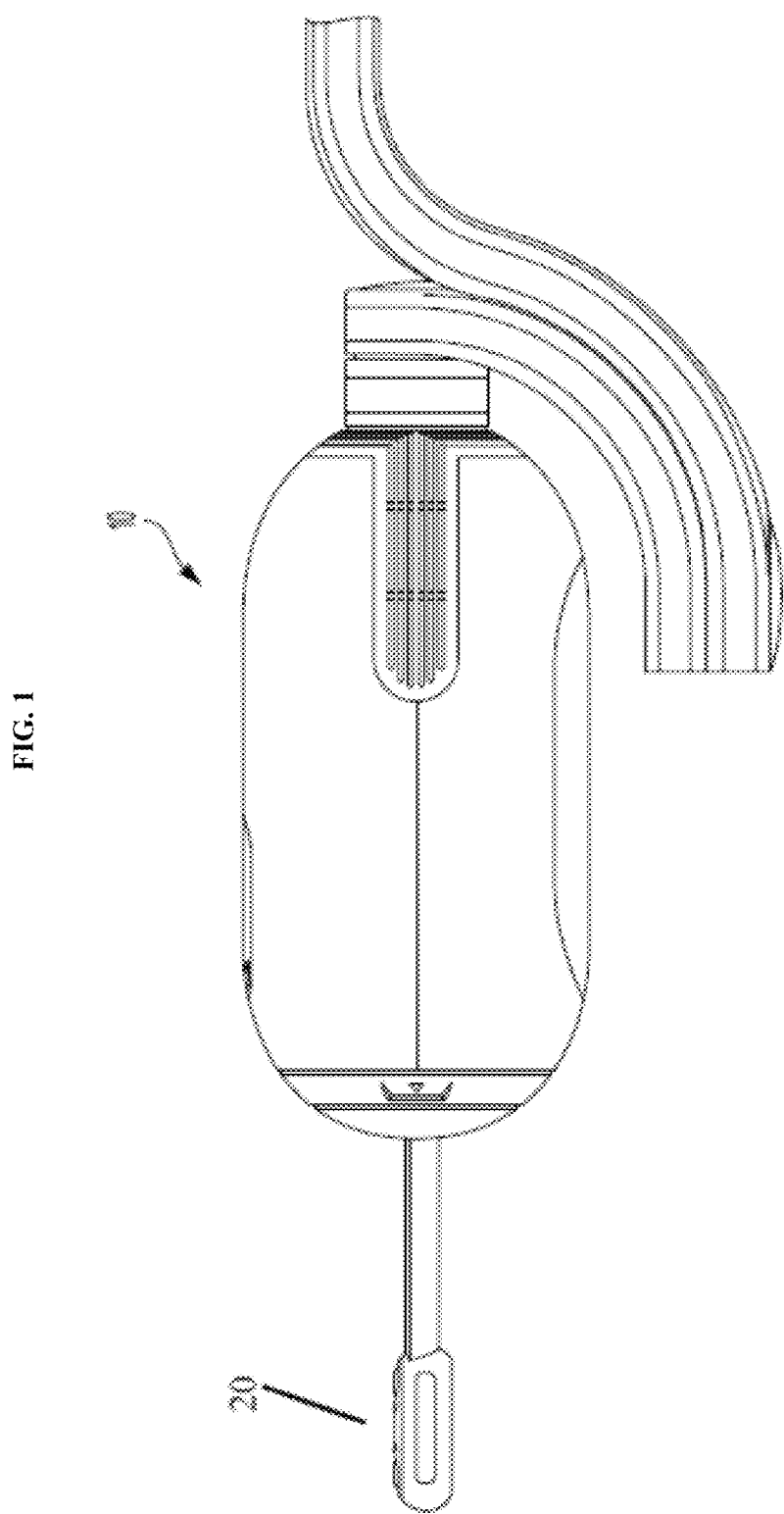
FIG. 1 shows a side view illustration of an exemplary automated dental drill (ADD) system, in accordance with an embodiment herein.
Figure 2:
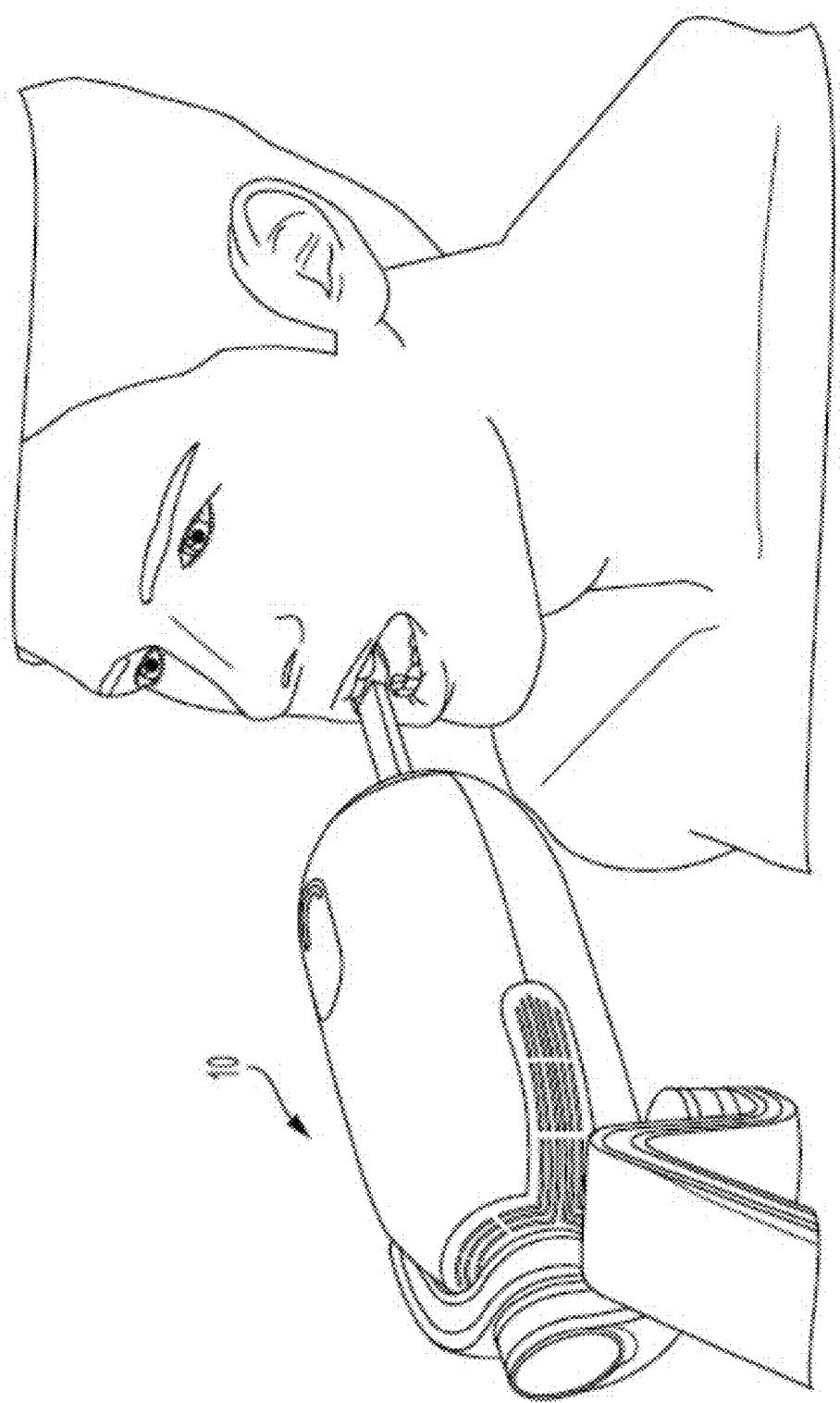
FIG. 2 shows a perspective view illustration of an exemplary ADD system treating a patient, in accordance with in embodiment herein.
Figure 3:
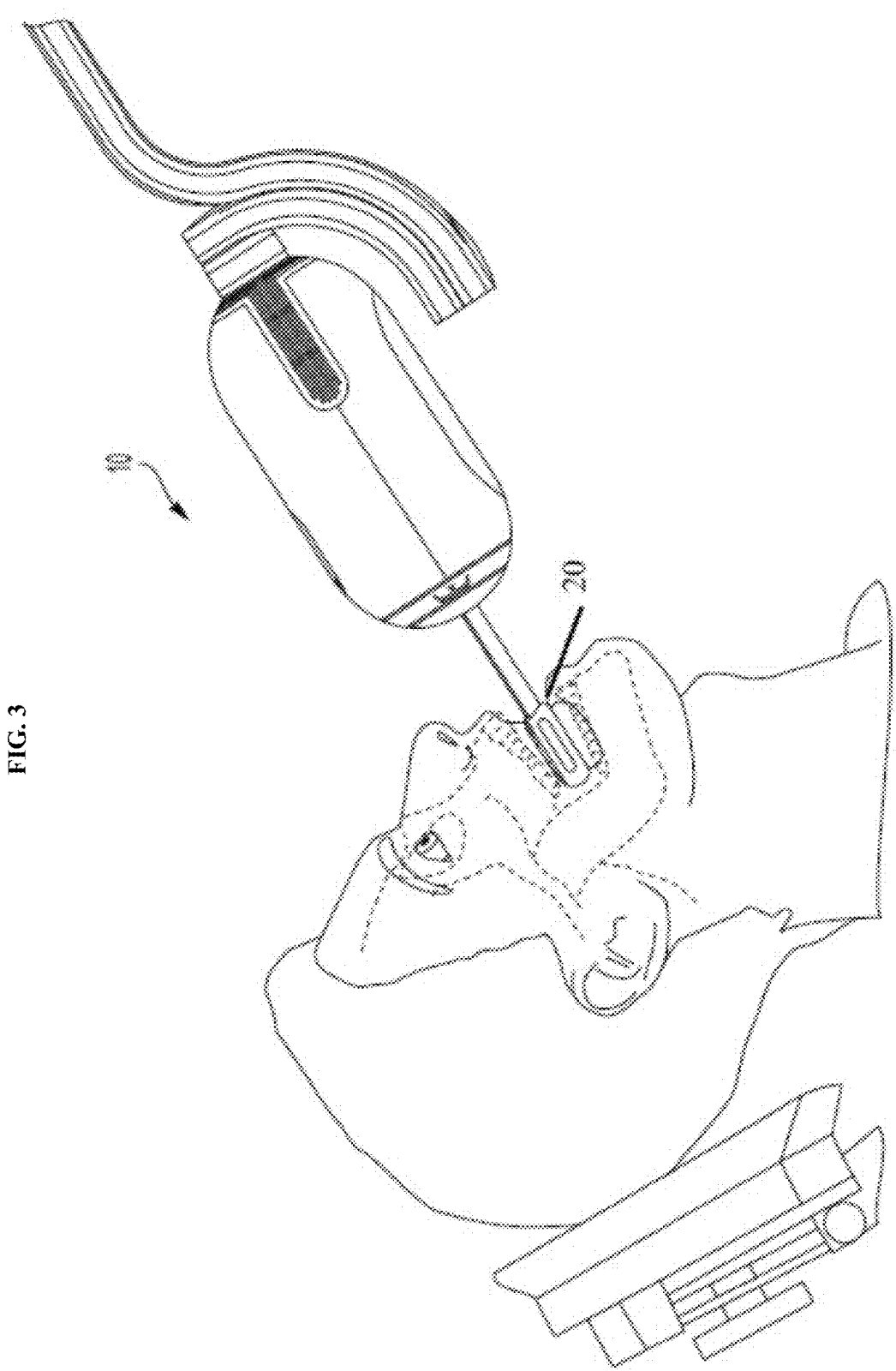
FIG. 3 shows a side cross sectioned view illustration of an exemplary ADD system treating a patient, in accordance with in embodiment herein.
Figure 4:
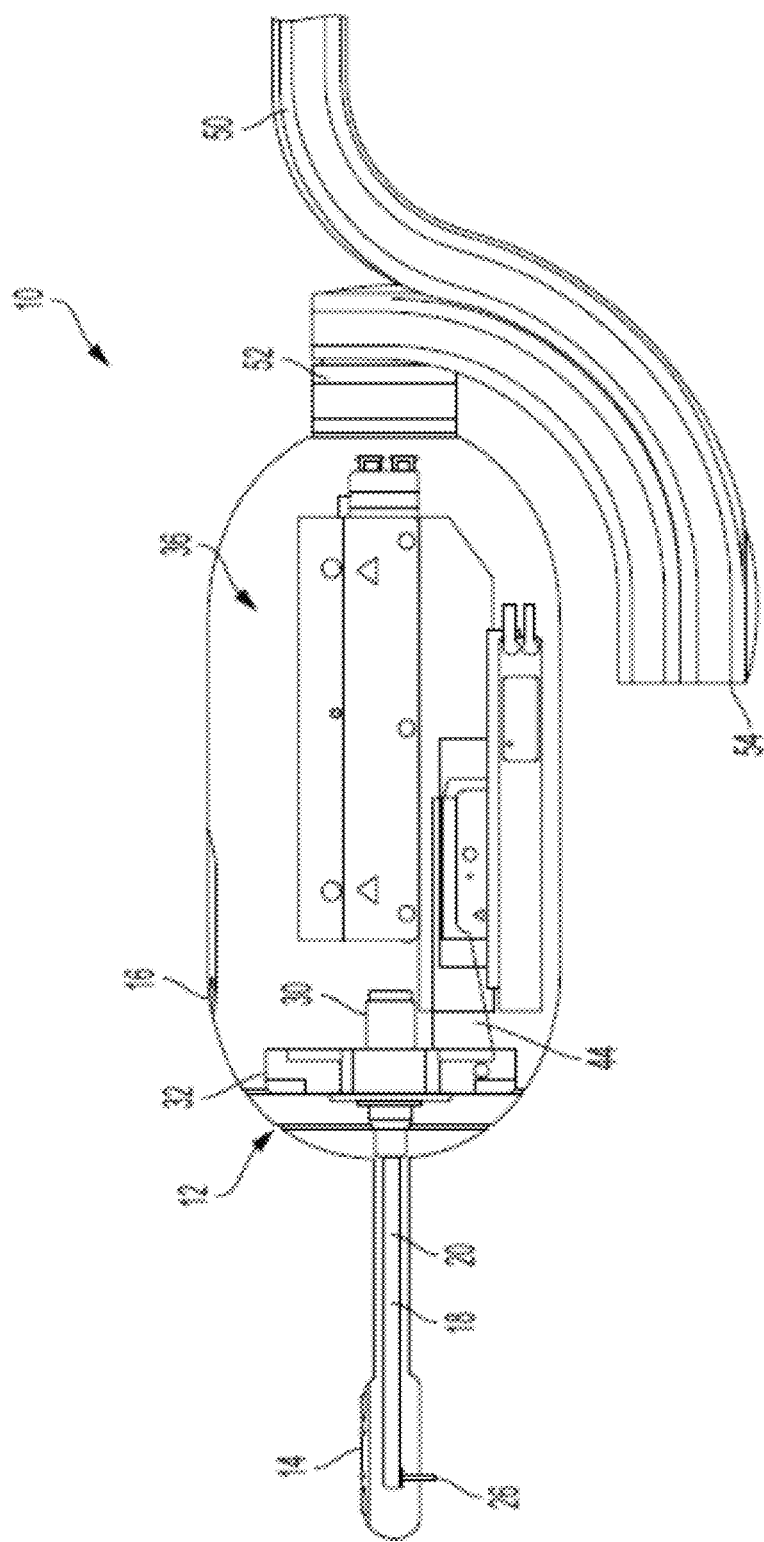
FIG. 4 shows a side cross sectioned view illustration of an exemplary ADD system, in accordance with in embodiment herein.
Figure 5:
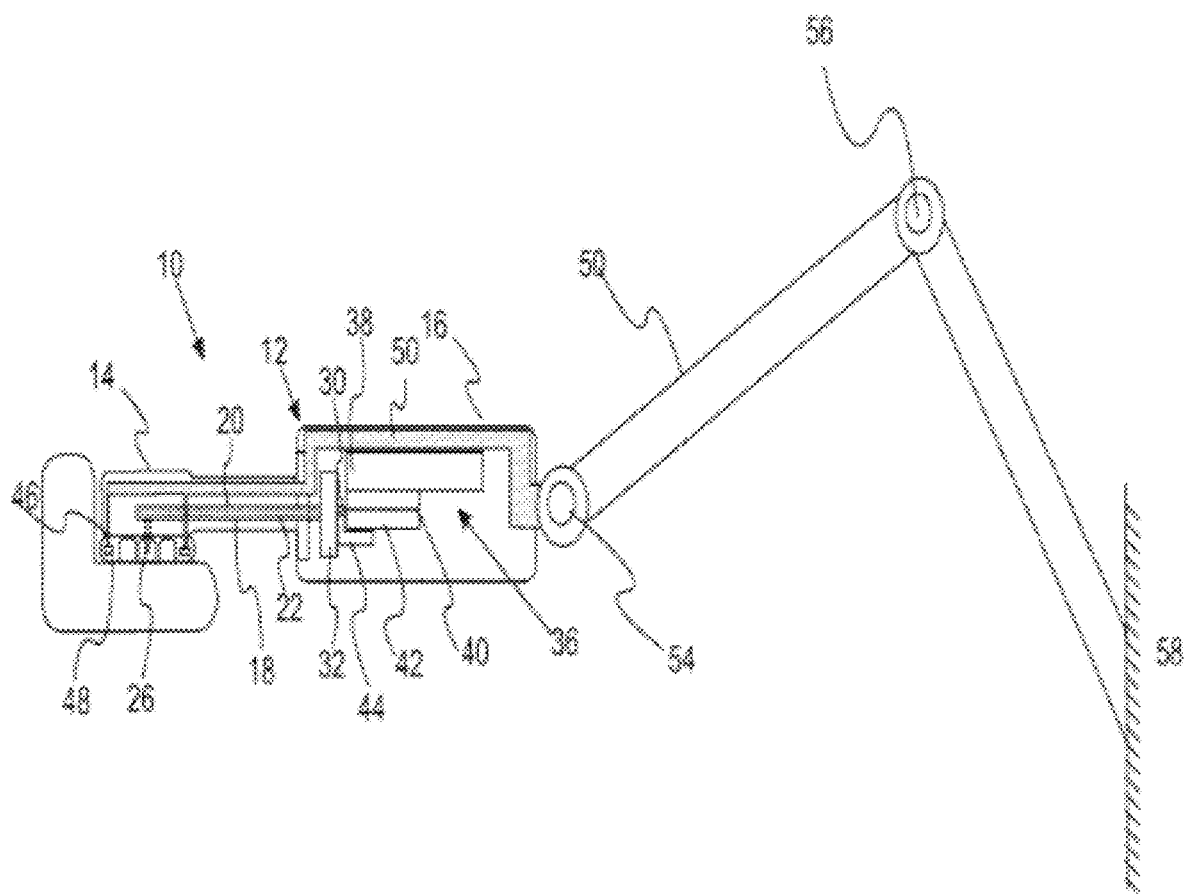
FIG. 5 shows a side view illustration of the components within an exemplary ADD system, in accordance with in embodiment herein.

FIGS. 4 and 5 show schematic illustrations of an automated drill are provided. The dental drill 10 can comprise a dental drill housing 12 which includes mouthpiece housing section 14 attached to drive housing section 16. The mouthpiece housing section 14 can be configured to at least be partially positioned in a subject's mouth during an operation. The end effector drive support 18 can be disposed in dental drill housing 12. At least a portion of end effector drive support 18 can be moveably positioned in mouthpiece housing section 14. The mouthpiece housing section 14 can comprise a shaft section 20 that extends into the mouthpiece housing section 14. In some embodiments, the shaft section 20 is hollow in order to allow coupling of the cutting mechanism driver to the end effector via a shaft 22.

Figure 12:
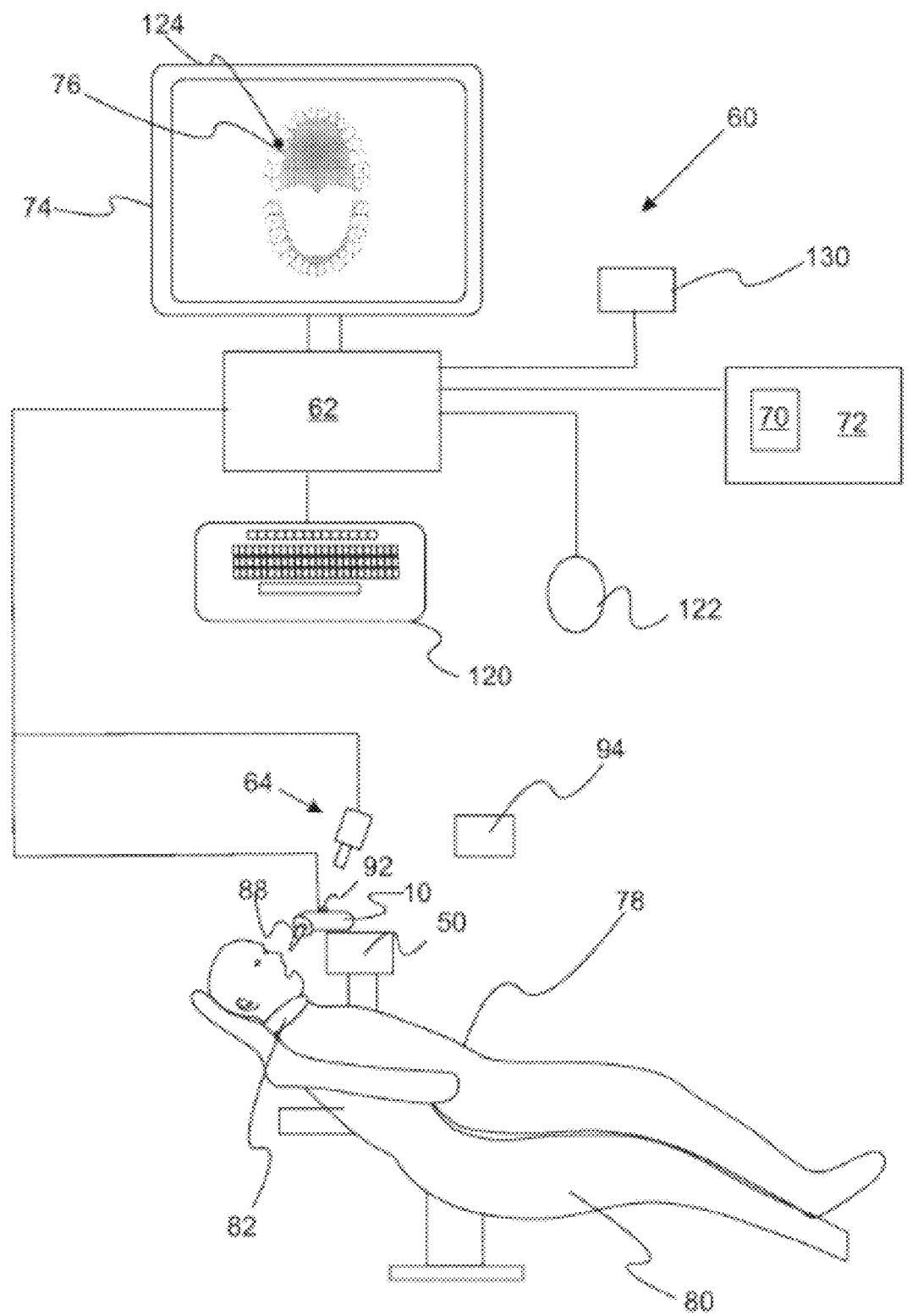
FIG. 12 shows an illustration of an exemplary dental treatment system, in accordance with an embodiment herein.

Further, per FIGS. 4, 5, and 12 the end effector 88 can be attached to end effector drive support 18 and can be moveable along three orthogonal linear directions (e.g., x, y, z) relative to mouthpiece housing section 14. Alternatively, the end effector 88 can be attached to end effector drive support 18 and can be moveable along six of more degrees of freedom relative to mouthpiece housing section 14. In operation, the z direction is defined as normal to the tooth. The x and y directions can be defined as being perpendicular to the z direction. Typically, the end effector 88 is located at the end of the end effector drive support 18. The end effector 88 can protrude from the mouthpiece housing section 14 and can be used for cutting of a native tooth, a dental appliance, or both to a desired tolerance and form. The cutting mechanism driver 30 can be coupled to the end effector 88 position. The end effector 88 can be positioned by the dental drill housing, through which a shaft can direct power to the end effector 88 (whether electromechanical for cutting burr, or electro-optical for cutting laser).

In some embodiments, the automated dental drill 10 further includes a drive assembly 36 which drives end effector 88 along the three or more directions. The drive assembly 36 can comprise three or more drives that move an end effector 88 in three or more directions: z-direction drive 38, y-direction drive 40, and x-direction drive 42. Each of the z-direction drive 38, the y-direction drive 40, and the x-direction drive 42 can be actuated by a stepper drive, piezoelectric drive, servomotor drive, or any combination thereof. Each of the z-direction drive 38, the y-direction drive 40, and the x-direction drive 42 can be a stepper drive, piezoelectric drive, servomotor drive, or any combination thereof. A coupler 44 can be used to couple the movement of the three drives to cutting drive support 18 and end effector 88 (e.g. whether electromechanical as with a cutting burr, or electro-optical as with a cutting laser). The system's end effector can be positioned in a plethora of ways to enable the removal of tooth tissue, and is enabled by but not limited to the degrees of freedom described herein.

In some embodiments, the automated dental drill 10 also comprises a clamp connector 46 that attaches to tooth clamp. The tooth clamp 48 can be attached to a subject's teeth about a tooth to be treated. The clamp connector 46 can be attached to support system 50 which is fixed to a dental drill housing 12. The clamp 48 can be fabricated from scanned data of the target teeth position and topography. Such data may be acquired from dental scanning devices (such as but not limited to use of a Dentsply Sirona CEREC or Align Technologies intraoral scanning device). The clamp 48 can reposition teeth to their original scanned position to correct for relative teeth movement between scanning and clamping when placed on the patient's teeth prior to cutting a given tooth. The drive assembly 36 can be zeroed to the clamp 48 before cutting. The drive assembly 36 can be mechanically coupled to the clamp 48 during cutting. In some embodiments, the tooth clamp 48 can be a 3D printed, molded or CNC machined structure having internal surfaces that mate with the teeth in an ultra-high precision fashion. During cutting, the end effector (e.g., the drill or laser) can cut through the plastic of the clam-shell structure, accessing the tooth material beneath. Since several teeth are held simultaneously by the tooth clamp internal surfaces, movement of the teeth can be reduced during cutting.

Figure 6:
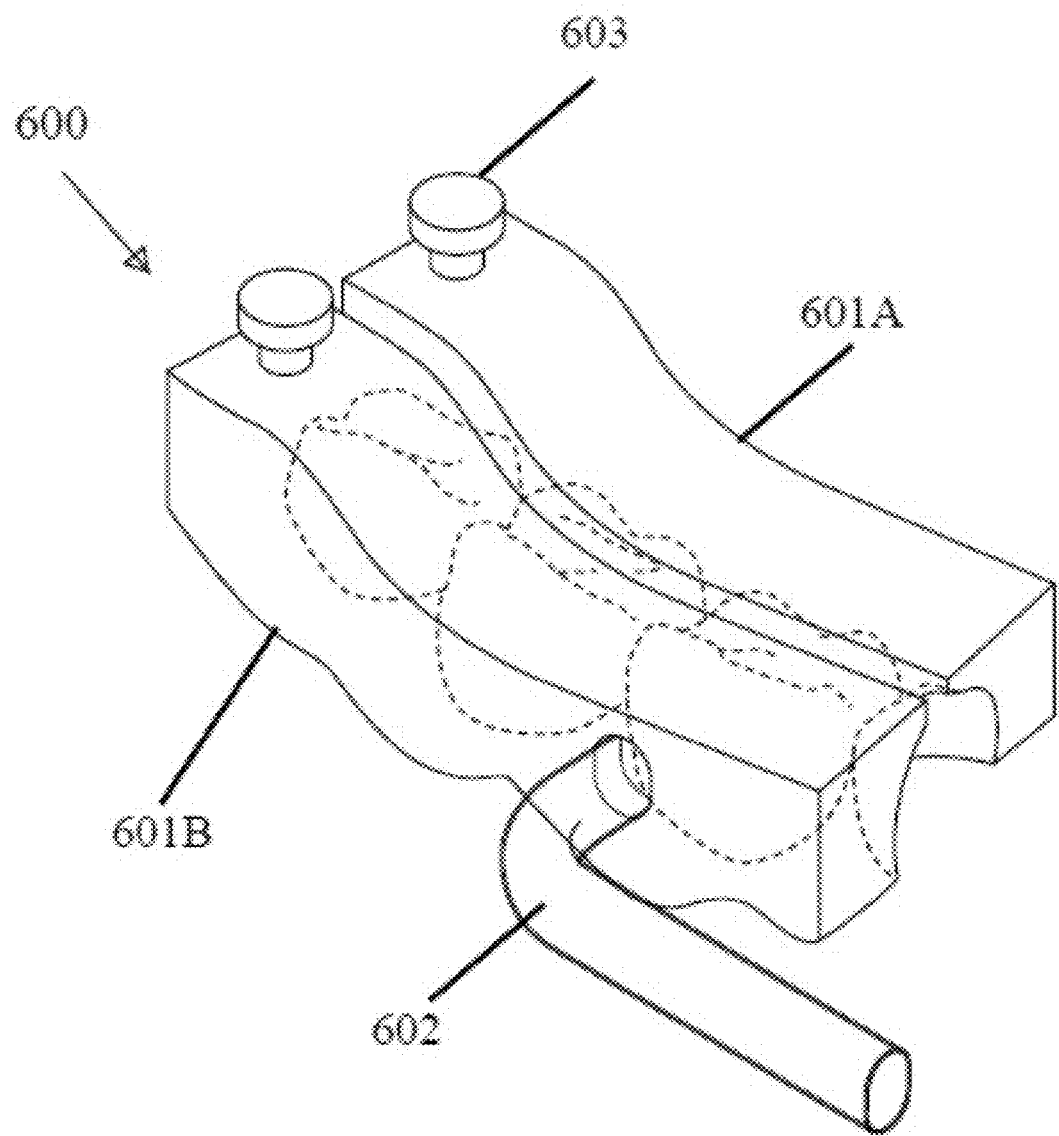
FIG. 6 shows an illustration of an exemplary first dental clamp, in accordance with an embodiment herein.
Figure 7:
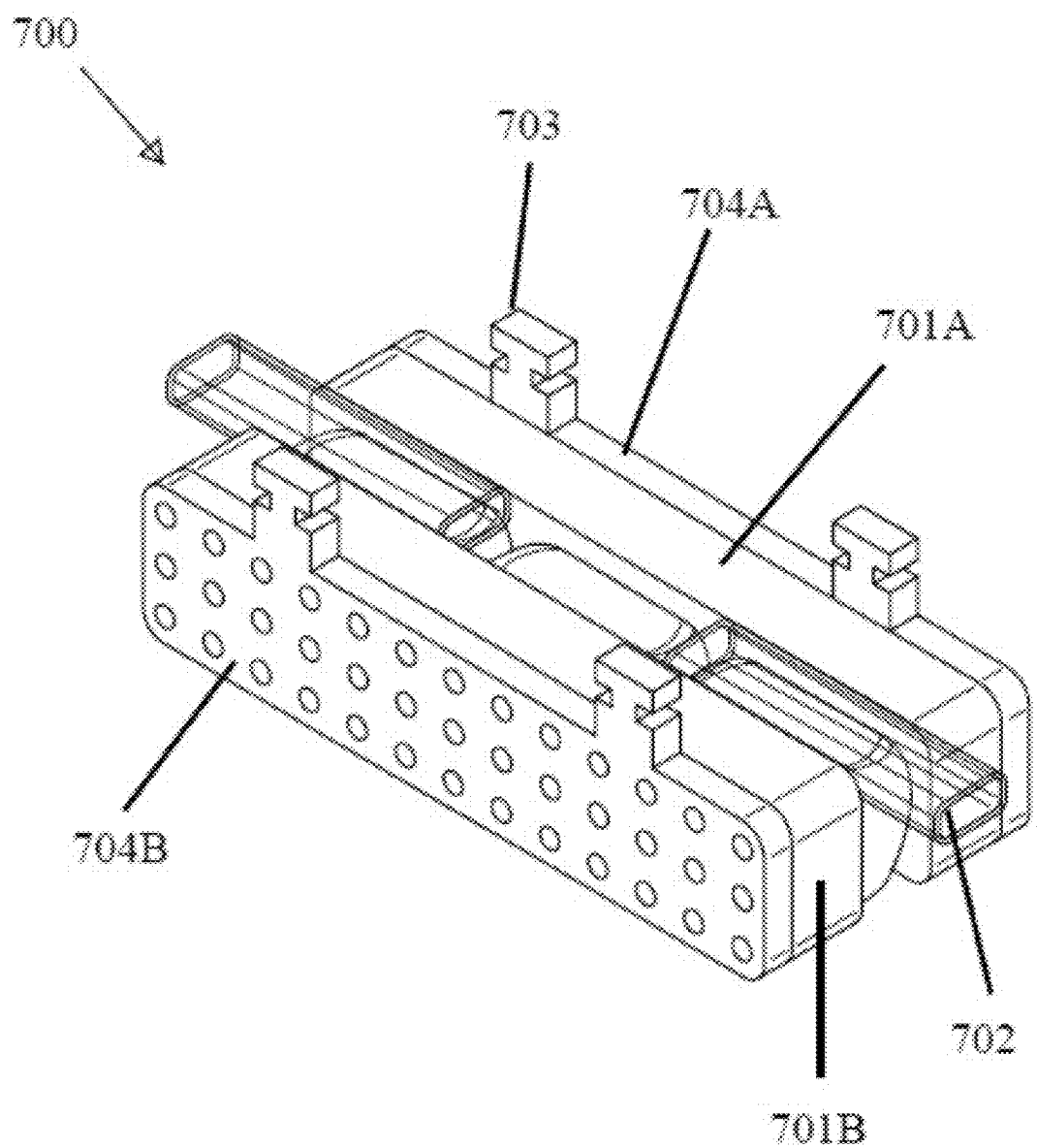
FIG. 7 shows an illustration of an exemplary second dental clamp, in accordance with an embodiment herein.
Figure 8:
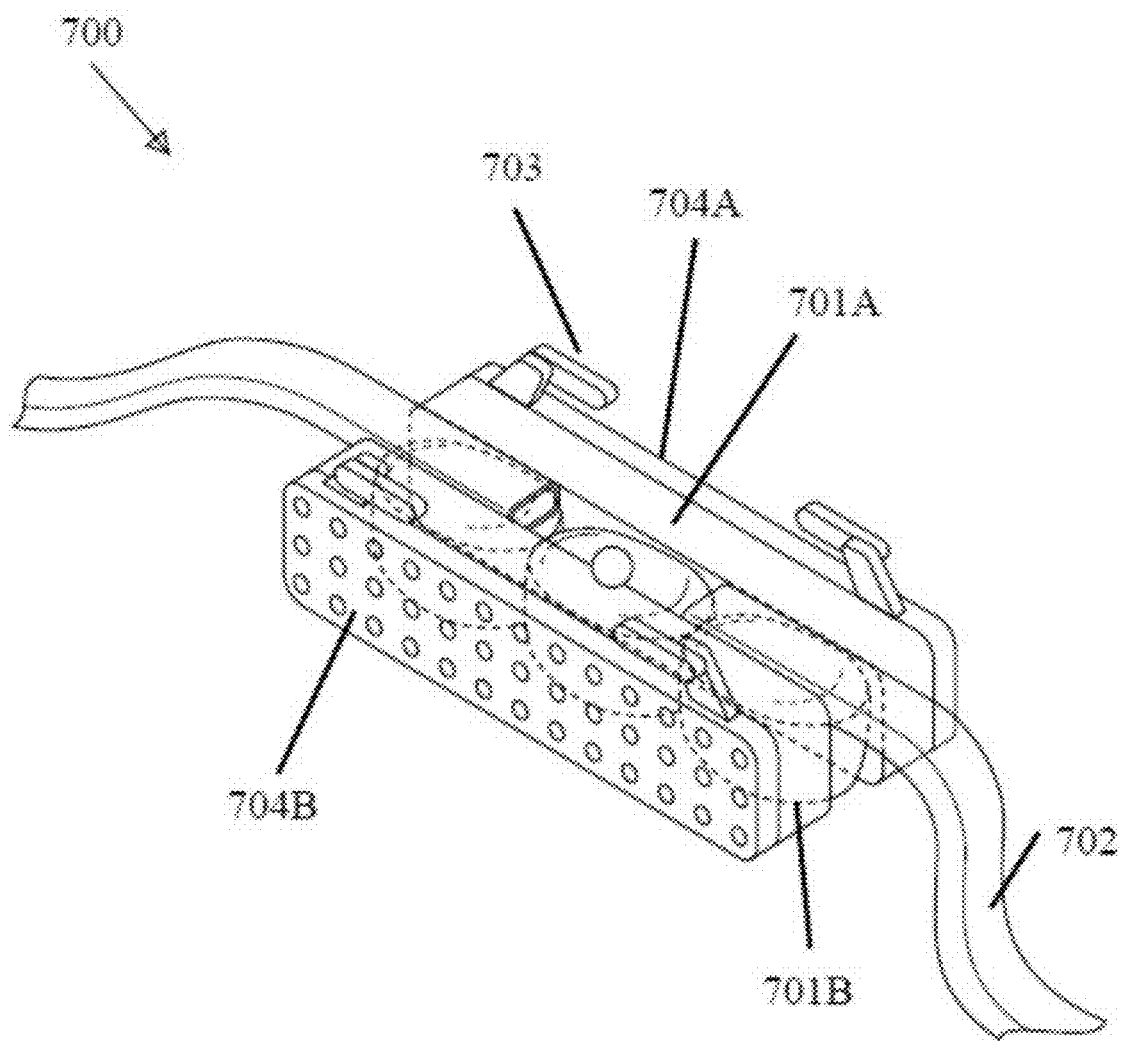
FIG. 8 shows an illustration of an exemplary third dental clamp, in accordance with an embodiment herein.
Figure 9:
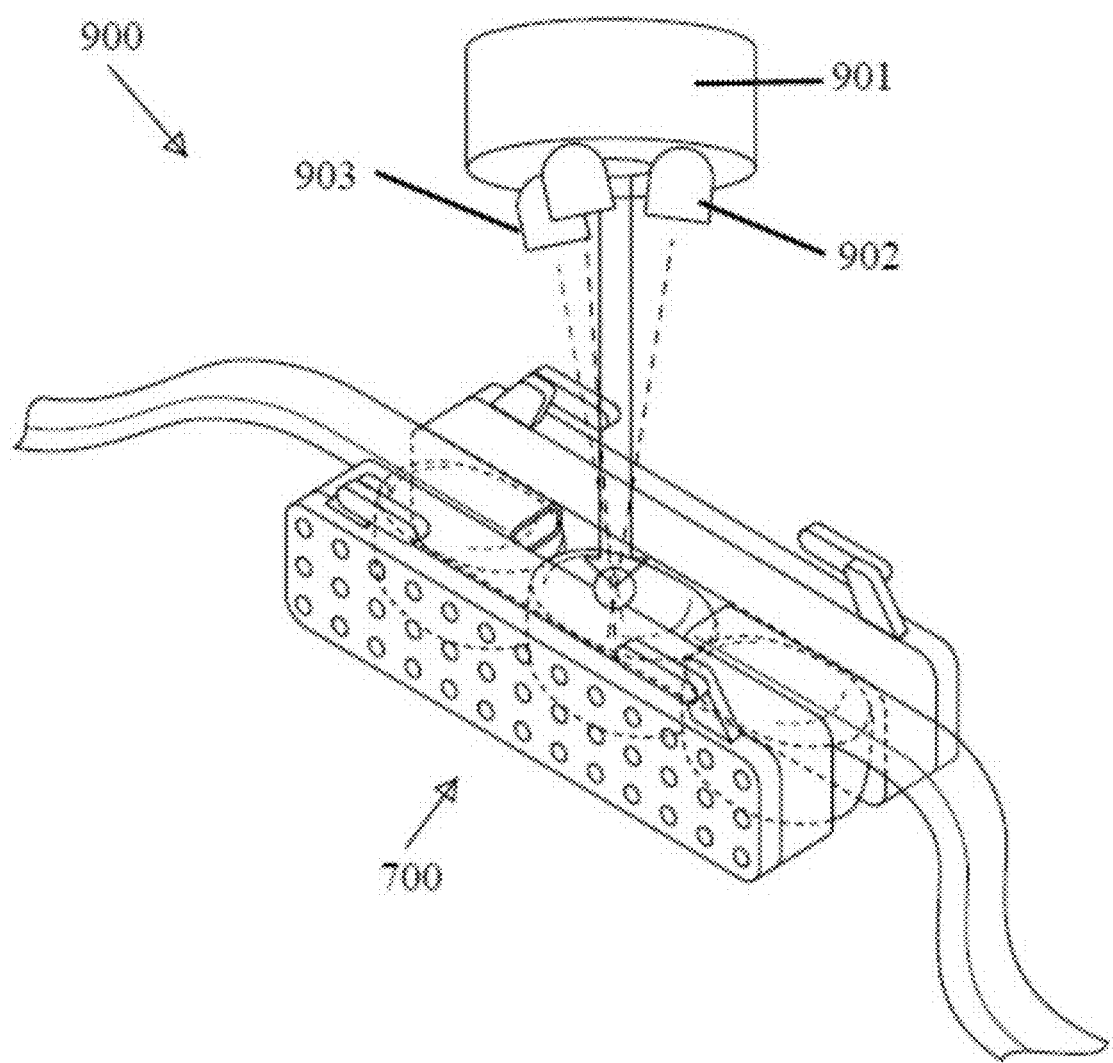
FIG. 9 shows an illustration of an exemplary first dental clamp, light guide, imaging sensor, and water flushing system, in accordance with an embodiment herein.
Figure 10:
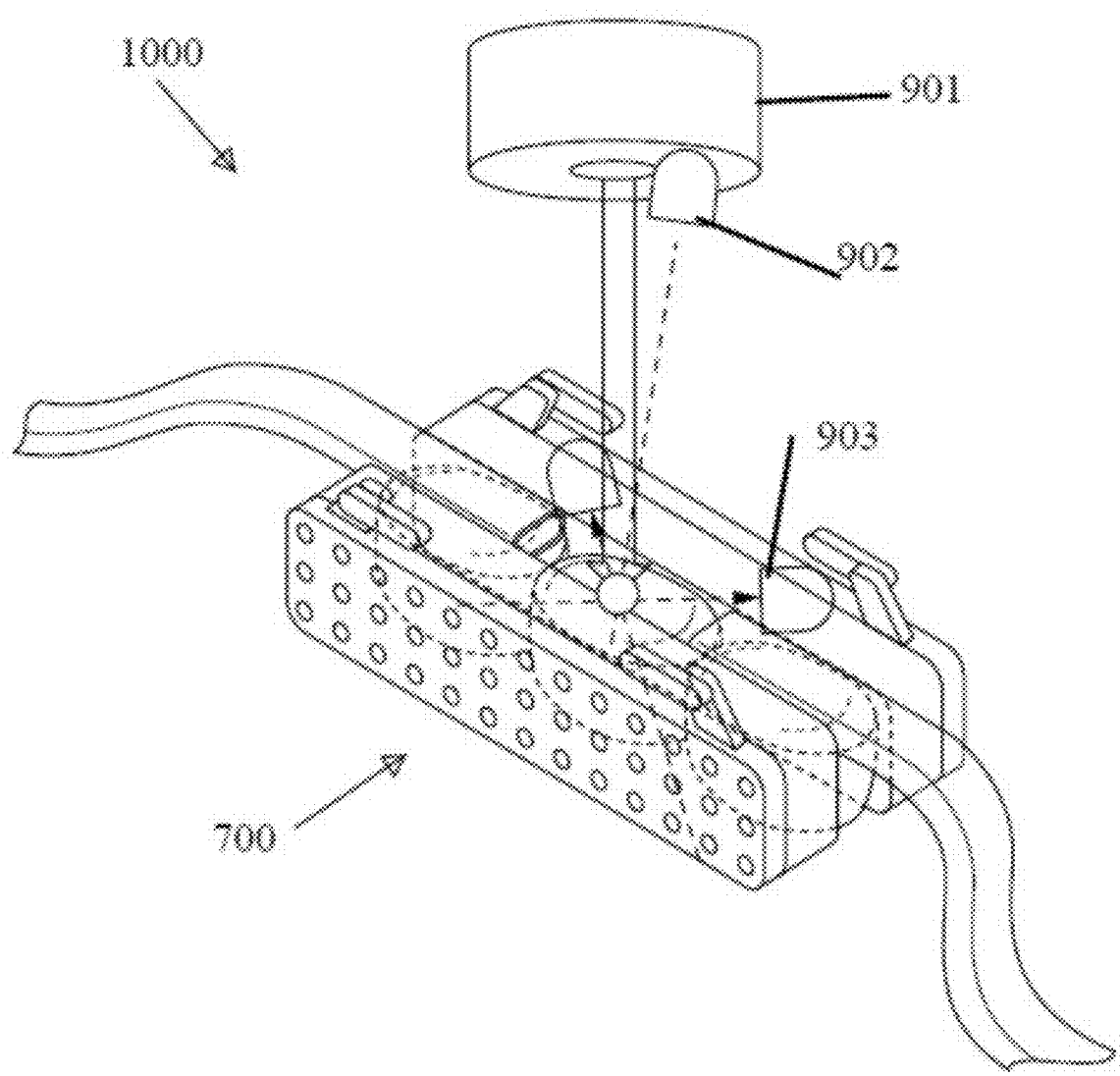
FIG. 10 shows an illustration of an exemplary second dental clamp, light guide, imaging sensor, and water flushing system, in accordance with an embodiment herein.
Figure 11:
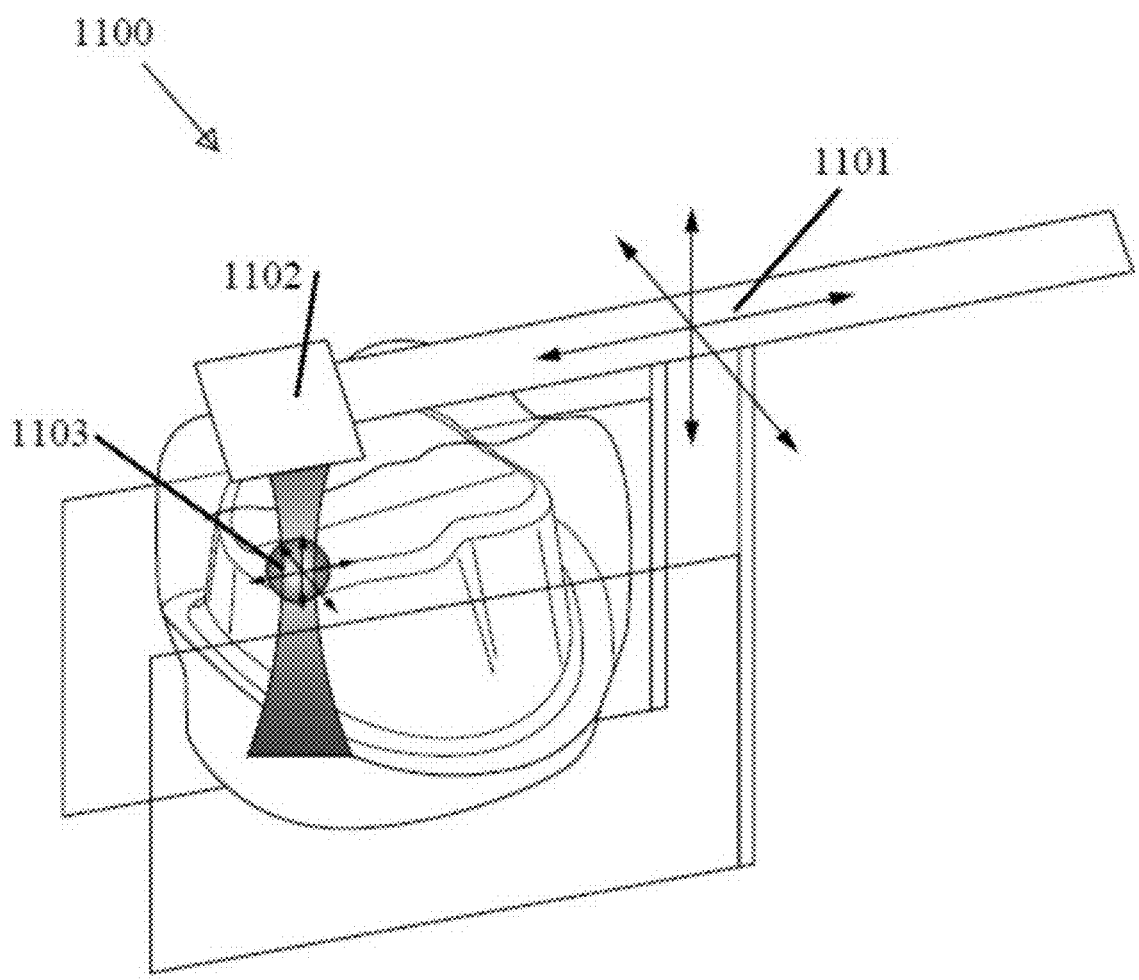
FIG. 11 shows an illustration of an exemplary laser ADD system, in accordance with an embodiment herein.

FIG. 6 shows an illustration of an exemplary first dental clamp. FIG. 7 shows an illustration of an exemplary second dental clamp. FIG. 8 shows an illustration of an exemplary third dental clamp. FIG. 9 shows an illustration of an exemplary first dental clamp, light guide, imaging sensor, and water flushing system. FIG. 10 shows an illustration of an exemplary second dental clamp, light guide, imaging sensor, and water flushing system. FIG. 11 shows an illustration of an exemplary laser ADD system.

In some embodiments, the automated dental drill 10 further includes a cantilever arm 50 and gimbals 52, 54, 56 that allow passive positioning and support of the automated dental drill. The cantilever arm 50 can be anchored to a support structure 58 (e.g., a wall, cart, ceiling, floor, dental chair, etc.).

Referring to FIG. 12, the dental treatment system 60 can include a central processing unit 62 in communication with tooth scanner 64 and automated dental drill 10. The automated dental drill 10 can be held by a user (i.e., a dentist) or mounted on a cantilever arm as set forth above. Per FIG. 12, treatment of the subject 78 can be performed while sitting in dental chair 80. The subject's 78 head can be immobilized and/or supported by a head restraint 82.

In some embodiments, the tooth scanner 64 includes a user handle for a user to hold and move the scanner as needed. A central processing unit 62 can control automated operation of the dental treatment system 60 monitor tooth cutting performance. The central processing unit can receive inputs from a force feedback mechanism that is used to monitor burr contact, indicating unplanned cutting, or to detect tooth decay. Additionally, positional information can be fed back from real time imaging of the cut surface during ablation procedures with a laser-based cutting system. Typically, the central processing unit 62 is contained in a computer work station. Control programs 70 which reside in computer memory 72 can be executed by the central processing unit 62 to receive image files from the tooth scanner 64 and to at least partially control the movement of automated dental drill 10. During operation, the tooth scanner 64 can transfer tooth image data to the central processing unit 62. The central processing unit 62 can include a display 74 on which the surgical process is guided through a series of onscreen prompts. The display 74 can render an image 76 of a target tooth of the subject 78 requiring surgical intervention from an image file.

The automated dental drill 10 can include an end effector 88 extending therefrom for performing dental surgery. In one embodiment, the end effector 88 is a dental burr. In another embodiment, end effector 88 is an optical element (such as a lens) to deliver and focus a laser beam on the treatment area. In another embodiment, the end effector 88 is a focused laser cutting region, adjusted by a movable lens. In some embodiments, the dental treatment system 10 includes a cantilever arm 50 which tracks the patient position and relays it to central processing unit 62. In some embodiments, the dental treatment system includes a cooling water jet that is used for position tracking, the water cooling jet providing an ultrasound signal or a light signal along a fiber optic axially down the cooling water jet to calculate distance to the target tooth.

End Effectors

In one embodiment, per FIG. 5, the end effector contains a motorized drill coupled to a motor 30. The dental drill 10 can also include a rotation drive 32 positioned in the dental drill housing, wherein the rotation drive 32 rotates the cutting drive support 18 and therefore the end effector 26 with respect to the mouthpiece housing section 14.

In some embodiments, the end effector emits laser radiation at one and/or a plurality of laser wavelengths selected for their ability to cut dental tissue, and is focused onto the work area using optical components (e.g. lenses, mirrors, fiber optic cables, or light pipes). For example, the laser beam includes an operating wavelength in the range from about 0.1 µm to about 50 µm. In variation, the laser beam has an operating wavelength within a range of wavelengths from about 1 µm to about 50 µm. In some embodiments, the laser beam has an operating wavelength within a range of wavelengths from about 5 µm to about 20 µm. In some embodiments, the laser beam has an operating wavelength within a range of wavelengths from about 6 µm to about 15 µm. In some embodiments, the laser beam has an operating wavelength within a range of wavelengths from about 0.1 µm to about 50 µm. In some embodiments, the laser beam operates at a plurality of wavelengths in the range from about 1 µm to about 50 µm. In some embodiments, the laser beam operates at a plurality of wavelengths in the range from about 5 µm to about 50 µm. In some embodiments, the laser beam operates at a plurality of wavelengths in the range from about 5 µm to about 20 µm.

In one embodiment, the laser generating source is located external to the end effector, within dental cutting head. In one variation, the laser generating source is located external to dental drill. In some embodiments, the laser is coupled to the end effector using an optical fiber and/or a plurality of fibers. In some embodiments, the laser is coupled to the end effector using a solid light guide. In some embodiments, the laser is coupled to the end effector using a hollow light guide. In some embodiments, the laser is coupled to the end effector using free-space optics (e.g. lenses and mirrors). In some embodiments, the laser generating source is located on or within the end effector (for example, a laser diode).

In some embodiments, the laser includes an isotopic $CO_2$ laser that vaporizes enamel. In some embodiments, the laser is configured to allow fast and efficient cutting at any angle, with more speed, precision and less bleeding than traditional cutting or drilling methods. In some embodiments, the system comprising a laser beam for tooth cutting or drilling does not require anesthesia of the subject. In some embodiments, the laser beam is configured to provide different spot size suitable for different cutting or drilling applications. In some embodiments, the laser beam is switched on and off in a pulsed, periodic manner during cutting. In some embodiments, the duration and time between "on" pulses may be controlled to optimize the cutting or drilling process. In some embodiments, the optical power of the laser beam generated herein may be controlled to optimize the cutting or drilling process. In some embodiments, the optic power of the laser beam generated herein may be varied from pulse to pulse in order to optimize the cutting or drilling process. In some embodiments, the optical power of the laser beam generated herein may be varied within a pulse in order to optimize the cutting or drilling process. In some embodiments, the laser-beam spot may be scanned within a localized region of the tooth, to optimize removal of tooth material at that region. In some embodiments, the laser-beam spot may be scanned within a localized region of the tooth, to optimize removal of gingiva at that region. In some embodiments, several or all of the spot size, spot scanning pattern, pulse repletion rate, pulse duration, pulse duty cycle, pulse firing system, and laser optical power may be controlled in concert to optimize the removal of tooth material. In some embodiments, several or all of the spot size, spot scanning pattern, pulse repletion rate, pulse duration, and laser optical power may be controlled in concert to optimize the removal of gingiva.

In a variation, the laser parameters are chosen such that the rate of tissue removal in one type of tissue is significantly higher than for other types of tissue, such that the other types of tissue are not significantly affected by the laser. For example, the laser parameters may be chosen such that the rate of tissue removal in soft tissue is ten times, one hundred times, or more higher than the rate of tissue removal in tooth enamel. As another example, the laser parameters may be chosen such that the rate of tissue removal in decayed tooth is ten times, one hundred times, or more higher than the rate of tissue removal in tooth enamel. In this manner, the laser may be made to effectively remove only the tissue type with the higher rate of tissue removal, while leaving the other tissue type predominantly unaffected.

In some embodiments, laser parameters are chosen such that the rate of tissue removal in one type of tissue is significantly higher than for other types of tissue, such that the other types of tissue are not significantly affected by the laser. For example, the laser parameters may be chosen such that the rate of tissue removal in soft tissue is ten times, one hundred times, or more higher than the rate of tissue removal in tooth enamel. As another example, the laser parameters may be chosen such that the rate of tissue removal in decayed tooth is ten times, one hundred times, or more higher than the rate of tissue removal in tooth enamel. In this manner, the laser may be made to effectively remove only the tissue type with the higher rate of tissue removal, while leaving the other tissue type predominantly unaffected.

In some embodiments, the laser generating source is an neodymium-doped yttrium aluminum garnet laser (neodymium YAG, Nd:YAG). In some embodiments, the laser generating source emits a light having a wavelength of about 0.946 μm. In some embodiments, the laser generating source emits a light having a wavelength of about 1.12 μm. In some embodiments, the laser generating source emits a light having a wavelength of about 1.32 μm. In some embodiments, the laser generating source emits a light having a wavelength of about 1.44 μm.

In some embodiments, the laser generating source is an erbium and chromium-doped yttrium aluminum garnet laser (erbium-chromium YAG, Er,Cr:YSSG). In some embodiments, the laser generating source emits a light having a wavelength of about 2.78 μm. In some embodiments, the laser generating source is an erbium-doped yttrium aluminum garnet laser (erbium YAG, Er:YAG). In some embodiments, the laser generating source emits a light having a wavelength of about 2.94 μm.

In some embodiments, the laser generating source is a carbon-dioxide laser. In some embodiments, the laser generating source emits a light having a wavelength of about 10 μm. In some embodiments, the laser generating source emits a light having a wavelength of about 10.6 μm. In some embodiments, the laser generating source emits a light having a wavelength of about 10.3 μm. In some embodiments, the laser generating source emits a light having a wavelength of about 9.6 μm. In some embodiments, the laser generating source emits a light having a wavelength of about 9.3 μm.

In some embodiments, the laser generating source emits a light having a wavelength of about 9.3 μm, nearing the peak absorption of hydroxyapatite. In some embodiments, the gain medium of the laser generating source is a carbon-dioxide gas that includes an oxygen-18 isotope. In some embodiments, the laser herein includes an isotopic CO2 laser that vaporizes enamel and gingiva. In some embodiments, the laser is configured to allow fast and efficient cutting at any angle, with more speed, precision and less bleeding than traditional cutting or drilling methods. In some embodiments, the system comprising a laser beam for tooth or gingiva cutting or drilling does not require anesthesia of the subject.

In some embodiments, the laser generating source is titanium-sapphire (Ti:Sapph) laser producing pulses of duration between about 10 fs and about 5 ps, with peak optical fluences sufficient to drive multi-photon ionization in dental tissue. In some embodiments, the laser generating source emits light of wavelength between about 0.65 μm and about 1.10 μm. In some embodiments, the laser generating source emits light of center wavelength of about 0.78 μm. In some embodiments, the laser generating source emits light of center wavelength of about 0.80 μm.

In some embodiments, the laser generating source is a fiber laser, consisting of Ytterbium-doped silica fiber producing pulses of duration between about 10 fs and about 5 ps, with peak optical fluences sufficient to drive multi-photon ionization in dental tissue. In some embodiments, the laser generating source emits a range of wavelengths between about 1.00 μm and about 1.20 μm. In some embodiments, the laser generating source emits light of center wavelength of about 1.03 μm. In some embodiments, the laser generating source emits light of center wavelength of about 1.04 μm.

In some embodiments, the laser generating source is a fiber laser, consisting of Ytterbium-doped silica fiber producing pulses of duration between about 10 fs and about 5 ps, with peak optical fluences sufficient to drive multi-photon ionization in dental tissue. In some embodiments, the laser generating source emits a range of wavelengths between about 1.45 μm and about 1.65 μm. In some embodiments, the laser generating source emits light of center wavelength of about 1.55 μm.

In some embodiments, the laser generating source is a fiber laser, consisting of Erbium-doped fluoride glass fiber producing pulses of duration between about 10 fs and about 5 ps, with peak optical fluences sufficient to drive multi-photon ionization in dental tissue. In some embodiments, the laser generating source emits a range of wavelengths between about 2.0 μm and about 4.0 μm. In some embodiments, the laser generating source emits light of center wavelength about 2.80 μm.

Scanning Systems

In one embodiment, per FIG. 12, the tooth scanner 64 includes a sensor system in which actuators and/or sensors are external to the automated dental drill 10. In FIG. 12, this external sensor system 94 visualizes the automated dental drill 10 and tracks its motion relative to the cut tooth. In some embodiments, the tooth scanner 64 determines the current conformation of the tooth as the procedure takes place, for comparison to the surgical plan. For example, a plurality of cameras 92 attached to automated dental drill 10. The plurality of cameras 92 provide two and/or three-dimensional images and/or live video of a subject's teeth to be mapped to a predetermined 3D surface scan of a surgical site thereby establishing a world coordinate system to which the segmented dental handpiece is registered. In one refinement, the plurality of cameras 92 includes millimeter scale cameras.

In some embodiments, the tooth scanner 64 includes sensors internal to the dental drill 10. In some embodiments, the tooth scanner may be mounted adjacent to the dental drill shaft. In some embodiments, the tooth scanner sensors may be mounted coaxially with the dental drill shaft in an annular configuration.

In some embodiments, when the end effector is a laser beam, the tooth scanner 64 includes optical sensors fed by light of a wavelength different than that used by the dental-drill actuator. In some embodiments, the optical scanners are fed by light counter-propagating with the laser beam, and split off to the sensor inputs using a beam splitter. In some embodiments, the optical scanners are fed by light that is neither co-propagating nor counter-propagating with the laser beam, and split off to the sensor inputs using a beam splitter. In some embodiments, the beam splitter is dichroic: reflecting only the optical wavelengths used by the tooth-scanner, and not the optical wavelength of the laser beam. In some embodiments, the tooth scanner may be mounted adjacent to the dental drill shaft. In other embodiments, the tooth scanner sensors may be mounted coaxially with the dental drill shaft in an annular configuration.

In one embodiment, the tooth scanner 64 includes a three-dimensional laser rangefinding system that measures the location of a plurality of points in the treatment area. In a variation, the three-dimensional laser rangefinding system includes a plurality of pulsed-laser time-of-flight rangefinders. In a variation, the three-dimensional laser rangefinding system includes a plurality of scattered-light sensors. In one embodiment, the scattered-light sensors use speckle holography to determine the location of a plurality of points on the tooth.

In a second variation, the three-dimensional laser rangefinding system includes an optical-coherence tomography (OCT) system. In some embodiments, this optical-coherence tomography rangefinding system may use white light interferometry to determine the range to a plurality of locations on the tooth. In other embodiments, this optical-coherence tomography rangefinding system may use frequency domain spatially encoded distance determination. In another embodiment, this optical-coherence tomography rangefinding system may use frequency domain temporally encoded distance determination.

In some embodiments, the tooth scanner 64 includes a three-dimensional ultrasound system. For example, the ultrasound system includes a plurality of ultrasound transducers and a plurality of ultrasound receivers. In yet another embodiment, the tooth scanner 64 includes a three-dimensional vision system. For example, the vision system may include a plurality of cameras.

In some embodiments, the current dimensions of the tooth as determined by the tooth scanner 64 are compared to prior dimensions of the tooth to determine the rate of tissue removal. In some embodiments, the prior dimensions of the tooth are determined using previous measurements by the sensors during the same procedure. In some embodiments, the prior dimensions of the tooth are determined using prior measurements of the tooth performed using other means which will be apparent to those knowledgeable in the art. As a nonlimiting example, teeth surface data is provided by a surface scanning system (such as but not limited to a Dentsply Sirona CEREC or Align Technologies intraoral scanning device).

In some embodiments, the current and past dimensions of the tooth are used to control the cutting speed of the automated dental drill (ADD) for optimal tissue removal. In some embodiments, the rate of tissue removal (as determined by current and past dimensions of the tooth) is used to distinguish healthy tissue from unhealthy tissue. As a nonlimiting example, dense tooth material will ablate at a lower rate than caries. In some embodiments, the rate of tissue removal (as determined by current and past dimensions of the tooth) is used to distinguish gingiva from tooth. In some embodiments, the spatial distribution of tissue-removal rate is used to determine the extent of tissue to be removed, and determine the progress and completion of the procedure.

In some embodiments, the determination of procedural progress or completion, as determined using the tissue-removal rate, is performed using an automated control system. As a nonlimiting example, the automated control system may be implemented using a computer. As another nonlimiting example, the automated control system may be implemented using a microcontroller. As a third nonlimiting example, the automated control system may be implemented using a Field-Programmable Gate Array (FPGA).

In other embodiments, in which the end effector is a laser beam, the laser beam is brought to a tight focus by an optical system such as a lens, holographic element, or the like, such that the laser beam irradiance is sufficiently high to remove tissue in only a small volume of space, while leaving tissue substantially unaffected outside said volume. In such an embodiment, the location of tissue removal is known absolutely by the physical laws of optics with respect to the location of the end of the lens which, itself, is attached to the drill arm. The size of the small volume of space in which tissue is removed is determined by the physical laws of optics with respect to the location of the end of the lens and by the optical properties characteristic of the specific tissue being removed. In this manner, knowledge of the location of the drill-arm position is sufficient to know the location of the tissue being removed. Said location may be changed by controllably changing the x-, y-, and z-positions of the drill arm. In another embodiment, the z-position of the focusing optical system may, instead, be changed to change the z-position of the tissue to be removed. In other embodiments, the z-position of both the drill arm and the focusing optical system may be changed in concert to change the z-position of the tissue to be removed. In such embodiments, the tooth scanner 64, while providing valuable diagnostic information on the progress of the procedure, is not required for the control of the cutting procedure.

Referring to FIG. 12, the operation of dental treatment system 60 is described as follows. Central processing unit 62 controls automated dental drill 10 to remove a region of the target tooth. Dental treatment system 60 includes input devices 120, 122 which can for example be a keyboard and mouse that receive surgical instructions from a user (i.e., dentist) for providing the surgical intervention. The instructions are received by the central processing unit 62. Characteristically, the surgical instructions including visual indications 124 on the image of a target tooth that are to be treated. Control program 70 guides the user through the dental protocols through a series of onscreen prompts (i.e., the user interface). In this context, actions attributable to control program 70 is understood to mean the execution of the relevant steps by central processing unit 62. In a variation, dental treatment system 60 includes static memory 130 for storing patient profiles and records which can be accessed by the user. In a refinement, central processing unit 62 also displays a load screen that shows a series of patient records and gives the option to load an existing patient, or create a new patient record.

In one embodiment, the tooth's cut surface is flushed with water during cutting from orifices surrounding the cutting head. Referring to FIG. 6, the water is then drawn away from the cutting region by means of a suction tube, attached onto a single orifice on the tooth clamp. In a variation, suction takes place through multiple suction tubes and orifices on the tooth clamp. In a variation, the tooth's surface is flooded with water from irrigation ports on the tooth clamp itself, and suction (as generalized above) is provided to draw away excess water. In an alternative embodiment, the tooth's cut surface does not require irrigation, due to the laser ablating tissue and fully vaporizing all materials. In all embodiments, suction is provided to draw away particulate, liquids, and gases formed from and during cutting activities.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

Computing System

Figure 13:
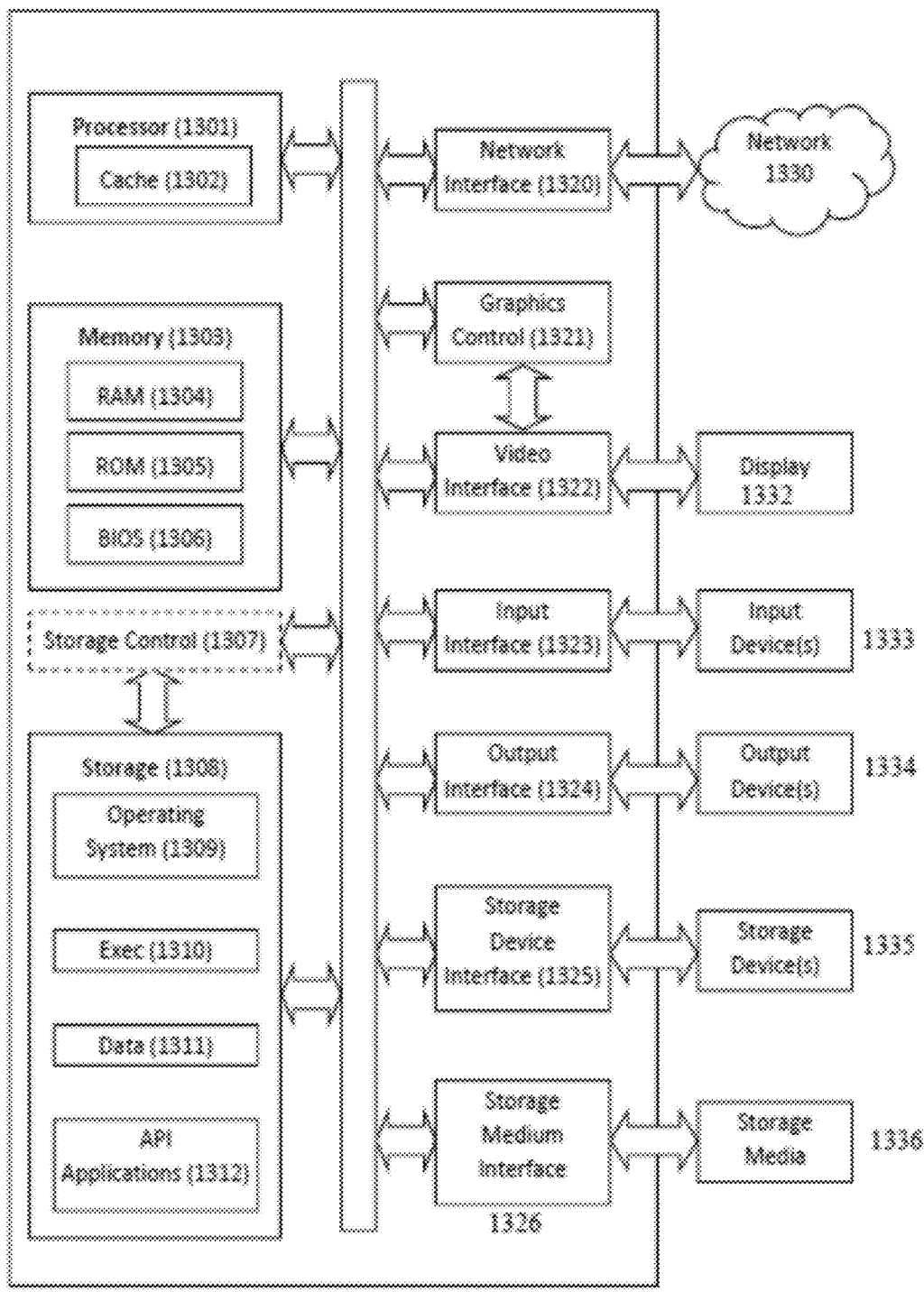
FIG. 13 shows a non-limiting example of a computing device; in this case, a device with one or more processors, memory, storage, and a network interface.

Referring to FIG. 13, a block diagram is shown depicting an exemplary machine that includes a computer system 1300 (e.g., a processing or computing system) within which a set of instructions can execute for causing a device to perform or execute any one or more of the aspects and/or methodologies for static code scheduling of the present disclosure. The components in FIG. 13 are examples only and do not limit the scope of use or functionality of any hardware, software, embedded logic component, or a combination of two or more such components implementing particular embodiments.

Computer system 1300 may include one or more processors 1301, a memory 1303, and a storage 1308 that communicate with each other, and with other components, via a bus 1340. The bus 1340 may also link a display 1332, one or more input devices 1333 (which may, for example, include a keypad, a keyboard, a mouse, a stylus, etc.), one or more output devices 1334, one or more storage devices 1335, and various tangible storage media 1336. All of these elements may interface directly or via one or more interfaces or adaptors to the bus 1340. For instance, the various tangible storage media 1336 can interface with the bus 1340 via storage medium interface 1326. Computer system 1300 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1300 includes one or more processor(s) 1301 (e.g., central processing units (CPUs) or general purpose graphics processing units (GPGPUs)) that carry out functions. Processor(s) 1301 optionally contains a cache memory unit 1302 for temporary local storage of instructions, data, or computer addresses. Processor(s) 1301 are configured to assist in execution of computer readable instructions. Computer system 1300 may provide functionality for the components depicted in FIG. 13 as a result of the processor(s) 1301 executing non-transitory, processor-executable instructions embodied in one or more tangible computer-readable storage media, such as memory 1303, storage 1308, storage devices 1335, and/or storage medium 1336. The computer-readable media may store software that implements particular embodiments, and processor(s) 1301 may execute the software. Memory 1303 may read the software from one or more other computer-readable media (such as mass storage device(s) 1335, 1336) or from one or more other sources through a suitable interface, such as network interface 1320. The software may cause processor(s) 1301 to carry out one or more processes or one or more steps of one or more processes described or illustrated herein. Carrying out such processes or steps may include defining data structures stored in memory 1303 and modifying the data structures as directed by the software.

The memory 1303 may include various components (e.g., machine readable media) including, but not limited to, a random access memory component (e.g., RAM 1304) (e.g., static RAM (SRAM), dynamic RAM (DRAM), ferroelectric random access memory (FRAM), phase-change random access memory (PRAM), etc.), a read-only memory component (e.g., ROM 1305), and any combinations thereof. ROM 1305 may act to communicate data and instructions unidirectionally to processor(s) 1301, and RAM 1304 may act to communicate data and instructions bidirectionally with processor(s) 1301. ROM 1305 and RAM 1304 may include any suitable tangible computer-readable media described below. In one example, a basic input/output system 1306 (BIOS), including basic routines that help to transfer information between elements within computer system 1300, such as during start-up, may be stored in the memory 1303.

Fixed storage 1308 is connected bidirectionally to processor(s) 1301, optionally through storage control unit 1307. Fixed storage 1308 provides additional data storage capacity and may also include any suitable tangible computer-readable media described herein. Storage 1308 may be used to store operating system 1309, executable(s) 1310, data 1311, applications 1312 (application programs), and the like. Storage 1308 can also include an optical disk drive, a solid-state memory device (e.g., flash-based systems), or a combination of any of the above. Information in storage 1308 may, in appropriate cases, be incorporated as virtual memory in memory 1303.

In one example, storage device(s) 1335 may be removably interfaced with computer system 1300 (e.g., via an external port connector (not shown)) via a storage device interface 1325. Particularly, storage device(s) 1335 and an associated machine-readable medium may provide non-volatile and/or volatile storage of machine-readable instructions, data structures, program modules, and/or other data for the computer system 1300. In one example, software may reside, completely or partially, within a machine-readable medium on storage device(s) 1335. In another example, software may reside, completely or partially, within processor(s) 1301.

Bus 1340 connects a wide variety of subsystems. Herein, reference to a bus may encompass one or more digital signal lines serving a common function, where appropriate. Bus 1340 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1300 may also include an input device 1333. In one example, a user of computer system 1300 may enter commands and/or other information into computer system 1300 via input device(s) 1333. Examples of an input device(s) 1333 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 1333 may be interfaced to bus 1340 via any of a variety of input interfaces 1323 (e.g., input interface 1323) including, but not limited to, serial, parallel, game port, USB, FIREWIRE, THUNDERBOLT, or any combination of the above.

In particular embodiments, when computer system 1300 is connected to network 1330, computer system 1300 may communicate with other devices, specifically mobile devices and enterprise systems, distributed computing systems, cloud storage systems, cloud computing systems, and the like, connected to network 1330. Communications to and from computer system 1300 may be sent through network interface 1320. For example, network interface 1320 may receive incoming communications (such as requests or responses from other devices) in the form of one or more packets (such as Internet Protocol (IP) packets) from network 1330, and computer system 1300 may store the incoming communications in memory 1303 for processing. Computer system 1300 may similarly store outgoing communications (such as requests or responses to other devices) in the form of one or more packets in memory 1303 and communicated to network 1330 from network interface 1320. Processor(s) 1301 may access these communication packets stored in memory 1303 for processing.

Examples of the network interface 1320 include, but are not limited to, a network interface card, a modem, and any combination thereof. Examples of a network 1330 or network segment 1330 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1330, may employ a wired and/or a wireless mode of communication. In general, any network topology may be used.

Information and data can be displayed through a display 1332. Examples of a display 1332 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 1332 can interface to the processor(s) 1301, memory 1303, and fixed storage 1308, as well as other devices, such as input device(s) 1333, via the bus 1340. The display 1332 is linked to the bus 1340 via a video interface 1322, and transport of data between the display 1332 and the bus 1340 can be controlled via the graphics control 1321. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 1332, computer system 1300 may include one or more other peripheral output devices 1334 including, but not limited to, an audio speaker, a printer, a storage device, and any combinations thereof. Such peripheral output devices may be connected to the bus 1340 via an output interface 1324. Examples of an output interface 1324 include, but are not limited to, a serial port, a parallel connection, a USB port, a FIREWIRE port, a THUNDERBOLT port, and any combinations thereof.

In addition or as an alternative, computer system 1300 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of operational and surgical information to assist in planning or execution of dental preparations undertaken by the automated dental drill system. information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

What is claimed is:

1. An automated dental drill system for performing a dental procedure on a patient, the automated dental drill system comprising:
    a processor;
    an end effector comprising a dental tool configured for disposition at least partially in the patient's mouth and to there perform an operation on a tooth of the patient;
    a tooth clamp configured to releasably rigidly attach to at least one tooth of the patient;
    a drive assembly configured to remain outside the patient's mouth throughout the entire dental procedure, wherein the drive assembly: (a) is controlled by the processor and (b) is configured to position the end effector with a first at least three degrees of freedom, relative to the tooth clamp;
    a clamp connector configured to connect to the tooth clamp to the drive assembly, such that, when the tooth clamp is coupled to the drive assembly and the tooth clamp is attached to the at least one tooth, position and orientation of the drive assembly remain fixed, relative to the at least one tooth;
    a support structure; and
    a passive cantilever arm having a second at least three degrees of freedom and being mechanically coupled between the support structure and the drive assembly to support the drive assembly.

2. The automated dental drill system of claim 1, wherein the processor is configured to receive an input from a feedback mechanism during the dental procedure.

3. The automated dental drill system of claim 2, wherein the feedback mechanism provides: force feedback; an indication of unplanned tooth cutting;
    an indication of tooth decay; positional information, or any combination thereof.

4. The automated dental drill system of claim 1, wherein the first at least three degrees of freedom comprises at least four degrees of freedom.

5. The automated dental drill system of claim 1, wherein the end effector comprises a drill.

6. The automated dental drill system of claim 1, wherein the end effector is configured to cut soft tissue.

7. The automated dental drill system of claim 1, wherein the drive assembly and end effector are configured to cut the tooth of the patient to a desired tolerance and form for receiving a crown, a partial crown, bridge, inlay, onlay, veneer, other restoration, or a prepared prosthetic tooth, or for a root canal.

8. The automated dental drill system of claim 1, wherein the end effector comprises: a laser, a probe, a nozzle, a pick, an x-ray, or any combination thereof.

9. The automated dental drill system of claim 1, further comprising an end-effector coupling comprising a gear, a shaft, a pulley, an optical fiber, a light guide, a free-space optic, a worm drive, a linear slide, a linear drive mechanism, a rotary mechanism, a mirror, a lens, a prism, or any combination thereof.

10. The automated dental drill system of claim 1, further comprising a multi-dimensional vision system comprising at least one of: a laser, an ultrasound transmitter, and visual optics, the multi-dimensional vision system being configured to provide at least one of: an at least two-dimensional image; a live video feed; and any combination thereof, of the tooth of the patient.

11. The automated dental drill system of claim 10, wherein at least one of the at least two-dimensional image and the live video feed is mapped to a predetermined 3D surface scan of a surgical site to establish a world coordinate system to which the end effector is registered and/or a material removal rate is tracked.

12. The automated dental drill system of claim 1, wherein the end effector is configured for tooth cutting.

13. The automated dental drill system of claim 1, wherein the first at least three degrees of freedom comprises at least five degrees of freedom.

14. The automated dental drill system of claim 1, wherein the first at least three degrees of freedom comprises at least six degrees of freedom.

15. An automated dental drill system for performing a dental procedure on a patient, the automated dental drill system comprising:
    a processor;
    an end effector comprising a dental tool configured to perform an operation on a target tooth of the patient;

a tooth clamp configured to rigidly attach to at least one tooth of the patient;

a drive assembly, which: (a) is controlled by the processor and (b) is configured to position the end effector with a first at least three degrees of freedom, relative to the tooth clamp;

a clamp connector, configured to connect the tooth clamp to the drive assembly, such that, when the tooth clamp is attached to the at least one tooth, position and orientation of the drive assembly remain fixed, relative to the at least one tooth;

a support structure; and a passive cantilever arm having a second at least three degrees of freedom and being mechanically coupled, at a proximal end thereof, to the support structure and, at a distal end thereof, to the drive assembly to support the drive assembly;

wherein, the tooth clamp, clamp connector, drive assembly and passive cantilever arm are configured such that, when the tooth clamp is attached to the at least one tooth, with the clamp connector connecting the tooth clamp to the drive assembly, the distal end of the passive cantilever arm is disposed outside of the mouth of the patient.

* * * * *